(12) United States Patent
Riley et al.

(10) Patent No.: US 9,108,906 B2
(45) Date of Patent: Aug. 18, 2015

(54) PRODUCTION OF ALKANE SULFONATES

(75) Inventors: Mark G. Riley, Hinsdale, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 403 days.

(21) Appl. No.: 13/427,204

(22) Filed: Mar. 22, 2012

(65) Prior Publication Data

US 2013/0253219 A1    Sep. 26, 2013

(51) Int. Cl.
C07C 309/00    (2006.01)
C07C 303/06    (2006.01)

(52) U.S. Cl.
CPC .................... C07C 303/06 (2013.01)

(58) Field of Classification Search
None
See application file for complete search history.

(56) References Cited

U.S. PATENT DOCUMENTS

| | | | |
|---|---|---|---|
| 2,631,980 A * | 3/1953 | Lewis | 510/452 |
| 3,743,673 A * | 7/1973 | Downer et al. | 562/121 |
| 3,803,058 A | 4/1974 | Marty | |
| 5,276,231 A | 1/1994 | Kocal et al. | |
| 7,250,530 B2 * | 7/2007 | Bagala et al. | 562/847 |
| 2009/0221464 A1 | 9/2009 | Tejero | |
| 2010/0282467 A1 | 11/2010 | Hutchison et al. | |

FOREIGN PATENT DOCUMENTS

| | | | | |
|---|---|---|---|---|
| EP | 2186784 | * | 1/2010 | C07C 5/333 |
| EP | 2186784 A2 | | 5/2010 | |
| GB | 1311245 | | 3/1973 | |
| RU | 2396254 C2 | | 8/2010 | |
| WO | 2011149789 A1 | | 12/2011 | |

OTHER PUBLICATIONS

International PCT Search Report for PCT/US2013/030310, mailing date Aug. 8, 2013.

* cited by examiner

*Primary Examiner* — Clinton Brooks

(57) ABSTRACT

A process for the production of olefin sulfonates is presented. The process comprising generating olefins from normal alkanes through a dehydrogenation unit to produce a mixture of alkanes and alkenes. The mixture is sulfonated to react the olefins and generate olefin sulfonates. The olefin sulfonates are separated from the normal alkanes to produce a product stream, with the normal alkanes recycled to the dehydrogenation unit.

19 Claims, 1 Drawing Sheet

PRODUCTION OF ALKANE SULFONATES

FIELD OF THE INVENTION

The present invention is directed to the process of generating alkylsulfonates. The production of alkylsulfonates are for the production of surfactants.

BACKGROUND OF THE INVENTION

Detergent range linear paraffins and linear olefins are typically produced using kerosene as a feedstock. While desirable carbon number chains vary, typical carbon number ranges for products are C10-C14, though at times it is desirable to produce heavier products, up to C18-C20 carbon number. Surfactants have other uses, and can require heavier hydrocarbon components. Generally, surfactants require both a water soluble characteristic and an oil soluble characteristic. These mixed properties enable surfactants to facilitate lowering of interfacial tension and the mixing and flowing of viscous liquids.

Surfactants have been used in chemical flooding systems for enhanced oil recovery processes. For enhanced oil recovery, higher molecular weight surfactants, or longer chained molecules are desirable. However, the production of surfactants is an expensive process. With increasing oil prices, the production has become more favorable, but producing surfactants through cheaper processes can improve the use of surfactants in enhanced oil recovery even at lower oil prices. Therefore, it is beneficial to seek improved and cheaper methods of producing surfactants.

SUMMARY OF THE INVENTION

The present invention provides for a cheaper process of generating heavy olefin sulfonates. Heavy olefin sulfonates are useful for surfactants in enhanced oil recovery processes. The process includes providing a heavy normal alkane stream in the C14 to C30 range. The heavy normal alkane stream is passed to a dehydrogenation reactor to generate an intermediate olefin stream. The intermediate olefin stream is degassed in a light gas separation unit, and passed to a selective hydrogenation unit to remove diolefins, and to generate a second intermediate olefin stream. The intermediate olefin stream does not separate out the unreacted paraffins, but passes the stream to a sulfonation unit, where the olefins are converted to olefin sulfonates, and generates an intermediate product stream. The olefin sulfonates are passed to an extraction unit where the olefin sulfonates are recovered in a product stream, and the n-alkanes are separated into a recycle stream. The n-alkanes are passed back to the dehydrogenation unit for further conversion to olefins.

In a preferred embodiment, the feedstream is passed to a fractionation unit for generating multiple feedstreams having a smaller range of carbon numbers. Each feedstream generated by the fractionation unit is passed to a parallel processing system, as described above, for converting the n-alkanes to olefin sulfonates.

Other objects, advantages and applications of the present invention will become apparent to those skilled in the art from the following detailed description and drawings.

DETAILED DESCRIPTION OF THE INVENTION

Figure 1:
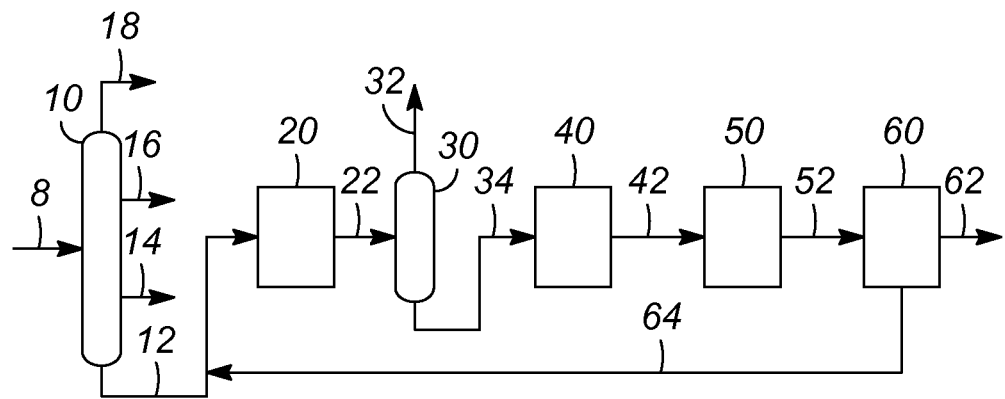
FIG. 1 is a design for the process of sulfonating heavy olefins.

The process of generating olefins from paraffins generally includes passing a process stream having the paraffins to a dehydrogenation unit to generate a process stream having olefins, and then separating the olefins from the paraffins through separation processes such as distillation. Distillation requires heating the process stream with olefins to a temperature sufficient to boil the components within the process stream. When the process stream comprises heavy hydrocarbons, the temperatures are greater to vaporize the hydrocarbons and lead to many problems in the process. Among the problems include thermal cracking of the hydrocarbons, which can significantly reduce yields and render the process uneconomical.

Alkylsulfonates, or olefin sulfonates, are useful as detergents, and are increasingly useful as surfactants in enhanced oil recovery processes. The olefin sulfonates for an enhanced oil recovery process preferably have long chained normal alkyl groups. However, cost is important, as the material is pumped into the ground and requires substantial quantities.

The present invention generates olefin sulfonates through a new process, can increase yields and saves energy and costs in the recovery of the product in a product stream. The process is a low cost method to manufacture olefin sulfonates from low cost paraffins. In particular, low cost Fischer-Tropsch paraffins in the C14 to C30 range are advantageous for this process. The process involves passing a feedstream of normal alkanes to a paraffin dehydrogenation unit, thereby generating a first effluent stream comprising olefins and light gases, as well as paraffins. The first effluent stream is passed to a separator to generate a light gas stream, and a second effluent stream comprising olefins and paraffins. The second effluent stream is liquid, and is passed to a selective hydrogenation unit to hydrogenate diolefins and generate an olefin process stream. The olefin process stream is passed to a sulfonation unit to sulfonate the olefins in the olefin process stream, thereby generating a sulfonate process stream. The sulfonate process stream is passed to an extraction unit to generate a first extract process stream comprising olefin sulfonates, and a second extract process stream comprising paraffins.

The process of sulfonating the stream comprising olefins and n-alkanes followed by separation is more economical than the normal process of separating the olefins from n-alkanes before sulfonation. This saves on the more expensive process of separating olefins from n-alkanes with little effect on the sulfonation process as the n-alkanes are relatively inert in the sulfonation process.

The second extract process stream can be passed back to the dehydrogenation unit for further conversion of unreacted paraffins. The second extract stream may contain small amounts of sulfates in the process stream from the extraction process. Due to the possibility of deleterious effects of sulfur compounds on the dehydrogenation catalyst, the second extract process stream can be passed to a sulfur removal unit to generate a substantially sulfur free second extract process stream, which is then passed to the dehydrogenation unit.

The dehydrogenation process can generate a small amount of aromatics. The aromatics can be removed by passing the olefin process stream to an aromatics extraction unit to generate the olefin process stream without aromatics. An aromatics process stream generate can be passed to other processing units. The olefin process stream with the aromatics removed is then passed to the sulfonation unit for converting olefins to olefin sulfonates.

The extraction process can be a liquid phase separation process. The sulfonate process stream can be combined with a water stream to form an aqueous phase and a non-aqueous phase. The aqueous phase will comprising the olefin sulfonates, which can be subsequently separated from the water through known processes. The non-aqueous phase will comprise mostly paraffins. The non-aqueous phase can be passed to a drying unit to remove residual water and to generate a dried paraffins stream. The dried paraffins stream is then passed to the dehydrogenation unit. The drying unit can comprise a molecular sieve, over which the non-aqueous phase is passed. The molecular sieve removes the water, and leaves a dried paraffin stream.

The hydrocarbon feedstream can be produced from several sources, with economics being a driving factor. In one embodiment, the feedstream comprising normal paraffins is generated from a heavy paraffin feedstock comprising heavy paraffins in the C14 to C30 range. The paraffin feedstock is passed to and adsorption separation unit to generate the feedstream comprising normal paraffins in the C14 to C30 range, and a raffinate stream comprising non-normal paraffins and other hydrocarbons. The feedstream is then passed to the dehydrogenation unit.

In a preferred embodiment, the paraffins are the C14 to C28 range. The dehydrogenation unit runs more efficiently when the paraffins have a more narrow distribution. The process can further include fractionating the normal paraffins feed stream to generate two or more effluent streams. The effluent streams from the fractionation unit are passed to the dehydrogenation unit. For molecular weights in the C14 to C28 range, the fractionation unit is normally operated as a vacuum fractionation unit, and operated at temperatures and pressures to provide for desired separations.

In one embodiment, the fractionation unit can comprise multiple fractionation towers, and the unit can generate multiple streams, or a more narrow range of n-paraffins can be chosen from the feed with a fractionation unit separating the desired carbon number range from the feedstream.

In one embodiment, the process is operated to select a narrower range of normal alkanes. The process includes passing the feedstream of normal alkanes in the C15 to C28 range to a fractionation unit. The fractionation unit is designed and operated to generate two or more streams of n-alkanes. The fractionation can be designed for a first stream comprising C15 to C18 n-alkanes, a second stream comprising C19 to C22 n-alkanes, a third stream comprising C20 to C24 n-alkanes, and a fourth stream comprising C24 to C28 n-alkanes.

The process can pass the individual streams to separate dehydrogenation reactors, or the first stream to a first dehydrogenation reactor, the second stream is passed to a second dehydrogenation reactor, the third stream is passed to a third dehydrogenation reactor, and the fourth stream is passed to a fourth dehydrogenation reactor, wherein each dehydrogenation reactor is operated to optimize the dehydrogenation process for the different feedstreams, with each dehydrogenation reactor effluent subsequently combined and processed through the light gas separation unit, the selective hydrogenation unit to remove diolefins, and the sulfonation unit. The dehydrogenation reactors are operated at different conditions, in particular different inlet temperatures, due to the different rates of conversion of the n-paraffins at different inlet temperatures.

The combined streams are then passed to a light gas separation unit to separate light gases from the olefin and n-paraffin process stream. The olefin and n-paraffin process stream is passed to a selective hydrogenation unit to selectively hydrogenate diolefins and acetylenes to generate an intermediate olefin stream. The intermediate olefin stream is passed to the sulfonation unit to form an olefin sulfonates process stream. The olefin sulfonate process stream is passed to an extraction unit to separation the olefin sulfonates from the unreacted n-alkanes, and the n-alkanes are passed back to the fractionation unit.

The process can include passing each n-alkane stream recovered from each extraction unit to a sulfur removal unit to generate a substantially sulfur free n-alkane stream. The substantially sulfur free n-alkane stream is passed back to the fractionation unit for converting the unreacted n-alkanes into the olefin sulfonates.

An alternative includes processing each stream in a rotation sequence, wherein the first stream is processed the dehydrogenation unit with the dehydrogenation unit effluent stream passed to the light gas separation unit, the selective hydrogenation unit, and the sulfonation unit. The second stream is then processed in the dehydrogenation unit with the effluent stream passed to the subsequent units in the overall process. The third stream and fourth stream can follow.

Another alternative depends upon the end use, and upon the selection of process stream or streams for generating an olefin sulfonate. As an example, if the plant only desires larger olefins, such as C24 to C28 olefins, the fractionation unit can be set to recycle or redirect the lighter n-alkanes to other process units, with the C24 to C28 n-alkanes passed to the dehydrogenation unit, and subsequent process units for forming the olefin sulfonates.

The choice and design of the number of dehydrogenation units can depend on the size of the process streams and the size of storage for intermittently storing unprocessed n-alkane streams. In one embodiment, the process can comprise multiple sets for processing each stream generated by the fractionation unit. The n-alkanes recovered in each stream therefore will only need to be passed back to the dehydrogenation unit, rather than back to the fractionation unit. When the conversion rate is low, the process can be more economical for processing each n-alkane stream with a narrow carbon range through a separate process stream wherein each process stream comprises the dehydrogenation unit, the light gas separation unit, the selective hydrogenation unit, the sulfonation unit, and the olefin sulfonate extraction unit.

The process is shown in FIG. 1 where an n-alkane feed 8, comprising C15 to C28 n-alkanes is passed to a fractionation unit 10. The fractionation unit 10 is operated to generate multiple process streams, a first stream 12, a second stream 14, a third stream 16 and a fourth stream 18. Each stream will follow a separate, but parallel path through parallel sets of equipment and process units. The first stream 12 is passed to a first dehydrogenation reactor 20 to generate a dehydrogenation reactor effluent stream 22. The dehydrogenation reactor effluent 22 is passed to a light gas separation unit 30 to separate hydrogen and other light gases in an overhead stream 32, and generates a second effluent stream 34. The second effluent stream 34 is passed to a selective hydrogenation unit 40 and generates an intermediate olefin process stream 42. The intermediate olefin process stream 42 is passed to a sulfonation unit 50 to generate a sulfonate process stream 52. The sulfonate process stream 52 is passed to an extraction unit 60 to generate a first process stream comprising olefin sulfonates 62 and a second extract stream comprising n-alkanes 64. The second extract stream 64 is passed to the dehydrogenation unit 20 for further processing of the unreacted paraffins. The process can include passing the second extract stream 64 through a sulfur removal unit prior to passing the second extract stream 64 to the dehydrogenation unit 20.

Figure 2:
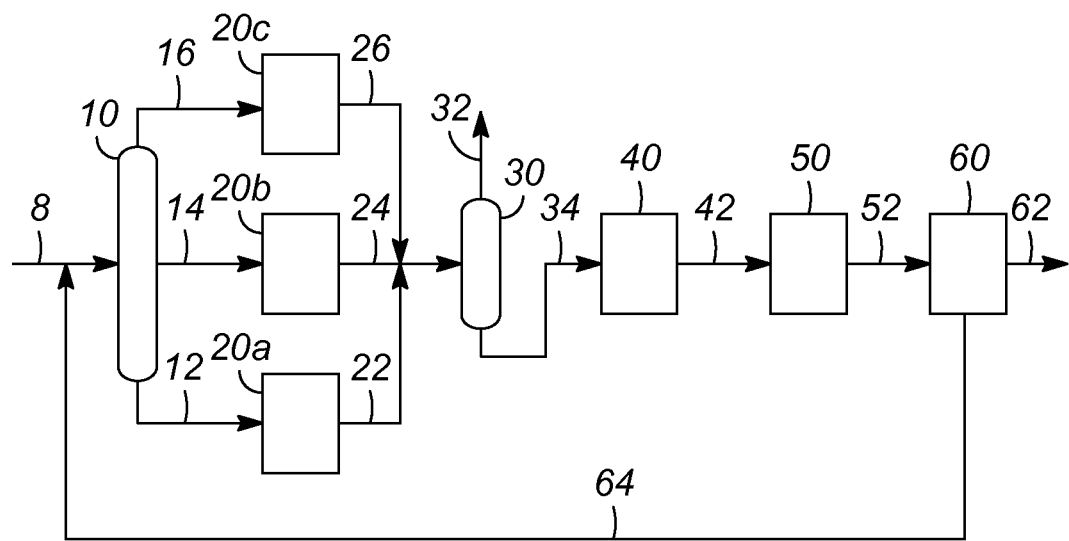
FIG. 2 is an alternate design for the process of sulfonating heavy olefins

Another embodiment of the process is shown in FIG. 2 where the n-alkane feed is split into three fractions. The process comprises passing C15 to C28 n-alkanes to a fractionation unit 10. The fractionation unit 10 is operated to generate three process streams, a first stream 12, a second stream 14, and a third stream 16. The first stream 12 is passed to a first dehydrogenation reactor 20a to generate a first dehydrogenation reactor effluent stream 22. The second stream is passed to a second dehydrogenation reactor 20b to generate a second dehydrogenation reactor effluent stream 24. The third stream is passed to a third dehydrogenation reactor 20c to generate a third dehydrogenation reactor effluent stream 26. The dehydrogenation reactor effluents 22, 24 and 26 are passed to a light gas separation unit 30 to separate hydrogen and other light gases in an overhead stream 32, and generates a second effluent stream 34. The second effluent stream 34 is passed to a selective hydrogenation unit 40 and generates an intermediate olefin process stream 42. The intermediate olefin process stream 42 is passed to a sulfonation unit 50 to generate a sulfonate process stream 52. The sulfonate process stream 52 is passed to an extraction unit 60 to generate a first process stream comprising olefin sulfonates 62 and a second extract stream comprising n-alkanes 64. The second extract stream 64 is passed to the fractionation unit 10 for further processing of the unreacted paraffins.

The dehydrogenation process has different operating conditions for different paraffins. The conversion is generally in the range from 10 to 15 percent of the n-alkanes converted to olefins. The dehydrogenation process includes operation under a pressure between 150 kPa and 400 kPa, with a preferred pressure between 200 kPa and 300 kPa, and a general operating pressure around 240 kPa. The LHSV is in the range from 10 to 40 hr-1, with a preferred range from 20 to 30 hr-1. The process is operated under a hydrogen rich atmosphere, with a hydrogen to hydrocarbon mole ratio (H2/HC) between 2 and 10, and preferably between 5 and 7. The operational temperature of the process is a function of average molecular weight, with the temperature declining for increasing average molecular weight. The operational temperature is the feed inlet temperature. For a feedstream in the C10 to C13 range, the range is 450° C. to 470° C., with a preferred operational inlet temperature of 460° C. For a feedstream in the C15 to C18 range, the range is 440° C. to 460° C., with a preferred operational inlet temperature of 450° C. For a feedstream in the C19 to C22 range, the range is 425° C. to 445° C., with a preferred operational inlet temperature of 435° C. For a feedstream in the C20 to C24 range, the range is 420° C. to 440° C., with a preferred operational inlet temperature of 430° C. For a feedstream in the C24 to C28 range, the range is 400° C. to 425° C., with a preferred operational inlet temperature of 414° C.

Other configurations can be imagined for this process, and the invention is intended to cover other variations of the processing of the n-alkane feedstream. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for generation olefin sulfonates comprising:
    passing a hydrocarbon feedstock comprising heavy paraffins in the C14 to C30 range to an adsorption separation unit to generate a feedstream comprising normal alkanes in the C14 to C30 range, and a raffinate stream;
    passing the feedstream comprising normal alkanes, wherein the alkanes have between 14 and 30 carbon atoms, to a paraffin dehydrogenation unit, thereby generating a first effluent stream comprising olefins and light gases;
    passing the first effluent stream to a separator to generate a light gas stream, and a liquid stream comprising olefins having 14 to 30 carbons atoms, thereby creating a second effluent stream;
    passing the second effluent stream to a selective hydrogenation unit to hydrogenate diolefins, and generate an olefin process stream;
    passing the olefin process stream to a sulfonation unit to sulfonate the olefins in the olefin process stream, and generate a sulfonate process stream; and
    passing the sulfonate process stream to an extraction unit to generate a first extract process stream comprising olefin sulfonates, and a second extract process stream comprising paraffins.

2. The process of claim 1 further comprising:
    passing the olefin process stream to an aromatics extraction unit to generate an olefin process stream without aromatics, and an aromatics process stream; and
    passing the olefin process stream without aromatics to the sulfonation unit.

3. The process of claim 1 further comprising passing the second extract process stream to the dehydrogenation unit.

4. The process of claim 1 wherein the alkanes have between 14 and 28 carbon atoms.

5. The process of claim 1 further comprising:
    passing the second extract process stream to a sulfur removal unit to generate a process stream with reduced sulfur content; and
    passing the free process stream to the dehydrogenation unit.

6. The process of claim 1 wherein the extraction process comprises:
    contacting the sulfonate process stream with water to generate a water effluent stream comprising the olefin sulfonates and an effluent stream comprising paraffins.

7. The process of claim 6 further comprising:
    passing the effluent stream comprising paraffins to a drying unit to remove residual water, thereby generating a dried paraffins stream; and
    passing the dried paraffins stream to the dehydrogenation unit.

8. The process of claim 1 further comprising:
    passing the feedstream comprising normal alkanes, wherein the alkanes have between 15 and 28 carbon atoms, to a fractionation unit, to generate two or more effluent streams; and
    passing the effluent streams to the dehydrogenation unit.

9. The process of claim 8 wherein the fractionation unit generates a first stream comprising C15 to C18 n-alkanes, a second stream comprising C19-C22 n-alkanes, a third stream comprising C20-C24 n-alkanes, and a fourth stream comprising C24-C28 n-alkanes, and wherein the first stream is passed to a first dehydrogenation reactor, the second stream is passed to a second dehydrogenation reactor, the third stream is passed to a third dehydrogenation reactor, and the fourth stream is passed to a fourth dehydrogenation reactor.

10. The process of claim 9 wherein the first, second, third, and fourth dehydrogenation reactors are operated at different operating conditions.

11. The process of claim 8 wherein the fractionation unit is vacuum fractionation column.

12. A process for generation olefin sulfonates comprising:
passing a feedstream comprising normal alkanes, wherein the alkanes have between 14 and 30 carbon atoms, to a fractionation column to generate a first stream comprising C15 to C18 n-alkanes, a second stream comprising C19-C22 n-alkanes, a third stream comprising C20-C24 n-alkanes, and a fourth stream comprising C24-C28 n-alkanes;
passing the stream to a first paraffin dehydrogenation unit, thereby generating a first dehydrogenation effluent stream comprising olefins and light gases;
passing the first dehydrogenation effluent stream to a separator to generate a light gas stream, and a liquid stream comprising olefins having 15 to 18 carbons atoms, thereby creating a first olefin effluent stream;
passing the first olefin effluent stream to a selective hydrogenation unit to hydrogenate diolefins, and generate a first olefin process stream;
passing the first olefin process stream to an aromatics extraction unit to generate an olefin process stream without aromatics, and an aromatics process stream;
passing the first olefin process stream to a sulfonation unit to sulfonate the olefins in the olefin process stream, and generate a first sulfonate process stream;
passing the first sulfonate process stream to an extraction unit to generate a first extract process stream comprising olefin sulfonates, and a second extract process stream comprising paraffins; and
passing the second extract process stream to the dehydrogenation unit.

13. A process for generation olefin sulfonates comprising:
a) passing a feedstream comprising normal alkanes, wherein the alkanes have between 14 and 30 carbon atoms, to a fractionation column to generate a first feedstream, wherein the feedstream comprises n-alkanes in the range selected from the group consisting of C15 to C18 n-alkanes, C19-C22 n-alkanes, C20-C24 n-alkanes, and C24-C28 n-alkanes;
b) passing the first feedstream comprising normal alkanes to a first paraffin dehydrogenation unit, thereby generating a first effluent stream comprising olefins and light gases;
c) passing the first effluent stream to a separator to generate a light gas stream, and a liquid stream comprising olefins, thereby creating a first olefin effluent stream;
d) passing the first olefin effluent stream to a selective hydrogenation unit to hydrogenate diolefins, and generate a first olefin process stream;
e) passing the first olefin process stream to an aromatics extraction unit to generate a first olefin product stream without aromatics, and an aromatics process stream;
f) passing the first olefin product stream to a sulfonation unit to sulfonate the olefins in the olefin product stream, and generate a sulfonate process stream;

g) passing the sulfonate process stream to an extraction unit to generate a first extract process stream comprising olefin sulfonates, and a recycle extract process stream comprising paraffins; and
h) passing the recycle extract process stream to the dehydrogenation unit.

14. The process of claim 13 further comprising:
passing the second extract process stream to a sulfur removal unit to generate a process stream with reduced sulfur content; and
passing the process stream to the dehydrogenation unit.

15. The process of claim 13 wherein the extraction process comprises:
contacting the sulfonate process stream with water to generate a water effluent stream comprising the olefin sulfonates and an effluent stream comprising paraffins.

16. The process of claim 13 further comprising a second feedstream from the group consisting of C15 to C18 n-alkanes, C19-C22 n-alkanes, C20-C24 n-alkanes, and C24-C28 n-alkanes, wherein the second feedstream is different from the first feedstream;
passing the second feedstream comprising normal alkanes to a second paraffin dehydrogenation unit, thereby generating a second effluent stream comprising olefins and light gases;
passing the second effluent stream to a separator to generate a light gas stream, and a liquid stream comprising olefins, thereby creating a second olefin effluent stream;
passing the second olefin effluent stream to a selective hydrogenation unit to hydrogenate diolefins, and generate a second olefin process stream;
passing the second olefin process stream to an aromatics extraction unit to generate a second olefin product stream without aromatics, and an aromatics process stream;
passing the second olefin product stream to a sulfonation unit to sulfonate the olefins in the olefin product stream, and generate a second sulfonate process stream;
passing the second sulfonate process stream to an extraction unit to generate a second extract process stream comprising olefin sulfonates, and a recycle extract process stream comprising paraffins; and
passing the recycle extract process stream to the dehydrogenation unit.

17. The process of claim 16 wherein the first and second dehydrogenation unit are the same unit operated at different times under different operating conditions.

18. The process of claim 16 further comprising selecting a third stream from the group consisting of C15 to C18 n-alkanes, C19-C22 n-alkanes, C20-C24 n-alkanes, and C24-C28 n-alkanes, wherein the third feedstream is different from the first feedstream and the second feedstream; and
processing the third feedstream through steps b) through h).

19. The process of claim 18 wherein the process conditions for the different feedstreams include different inlet feed temperatures to the dehydrogenation reactor.

* * * * *